(12) United States Patent
Wallace et al.

(10) Patent No.: US 6,447,462 B1
(45) Date of Patent: Sep. 10, 2002

(54) URODYNAMIC CATHETER AND METHODS OF FABRICATION AND USE

(75) Inventors: Wm. Dean Wallace, Salt Lake City; Christopher A. Cutler, Centerville; Steven R. Smith, Draper; Richard A. Dixon, West Jordan, all of UT (US)

(73) Assignee: Clinical Innovation Associates, Inc., Murray, UT (US)

( * ) Notice: Subject to any disclaimer, the term of this patent is extended or adjusted under 35 U.S.C. 154(b) by 0 days.

(21) Appl. No.: 09/504,972

(22) Filed: Feb. 15, 2000

(51) Int. Cl.[7] .................................................. A61B 5/00
(52) U.S. Cl. ........................ 600/561; 600/435; 604/915
(58) Field of Search ................................ 600/568–589, 600/588, 591, 433, 434, 435, 585; 606/192, 193; 604/915, 919, 920

(56) References Cited

U.S. PATENT DOCUMENTS

| | | | | |
|---|---|---|---|---|
| 3,884,242 A | 5/1975 | Bazell et al. | ........... | 128/207.15 |
| 4,019,505 A | 4/1977 | Kornblum et al. | ..... | 604/101.05 |
| 4,077,394 A | 3/1978 | McCurdy | ..................... | 600/18 |
| 4,301,811 A | 11/1981 | Layton | ........................ | 600/561 |
| 4,776,347 A | 10/1988 | Matthews | ................... | 600/587 |
| 4,901,735 A | 2/1990 | von Berg | .................... | 600/561 |

FOREIGN PATENT DOCUMENTS

| | | |
|---|---|---|
| EP | 0 846 472 A1 | 6/1998 |
| EP | 0 972 535 A2 | 1/2000 |
| GB | 968376 | 9/1964 |
| GB | 2 318 513 A | 4/1998 |
| WO | WO 011/12003 | 3/2000 |

OTHER PUBLICATIONS

Tanagho, Emil A., M.D., et al., "Membrane Catheter," *Urology*, Aug. 1977, vol. X. No. 2, pp. 173–176.
The Fundamentals of Female Urodynamic Study Interpretation: Case Studies Using the LuMax™ Fiber Optic Cystometry System, ©1997, MedAmicus, Inc.
PCT International Search Report, PCT/US01/04749, dated Jul. 27, 2001.

*Primary Examiner*—Kevin Shaver
*Assistant Examiner*—Charles Marmor, II
(74) *Attorney, Agent, or Firm*—TraskBritt

(57) ABSTRACT

A urodynamic catheter incorporating at least one balloon adjacent a distal end thereof and associated with a pressure lumen extending to a proximal end to be placed external to the body of a patient and usable with a transducer housing including a pressure transducer and a mechanism for alternatively venting an air column defined by the assembled pressure lumen and transducer housing to the ambient environment and closing the air column and charging it with air while reducing volume of the air column. One embodiment includes two, separately-chargeable balloons and a bladder fill tube, another embodiment includes a single balloon and a fill tube, and yet another embodiment, suitable for use as a reference catheter to measure abdominal pressure, includes only a single balloon and omits the fill tube. A novel catheter architecture and assembly technique are also disclosed, as are methods of using the inventive catheter.

49 Claims, 5 Drawing Sheets

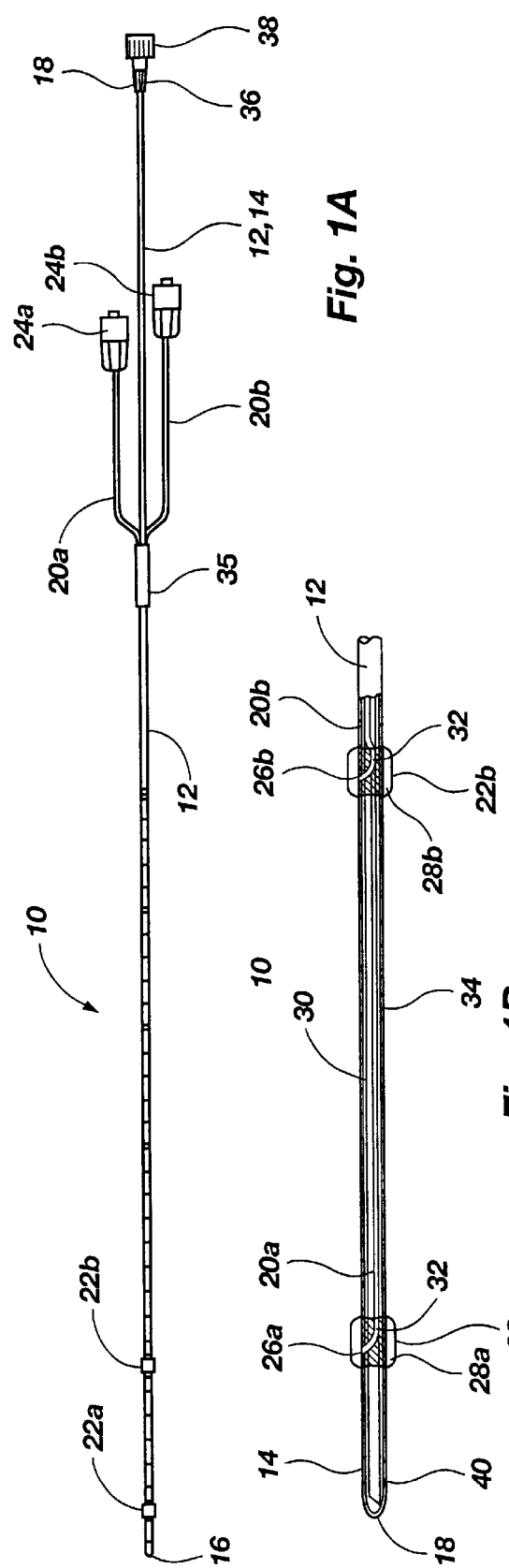
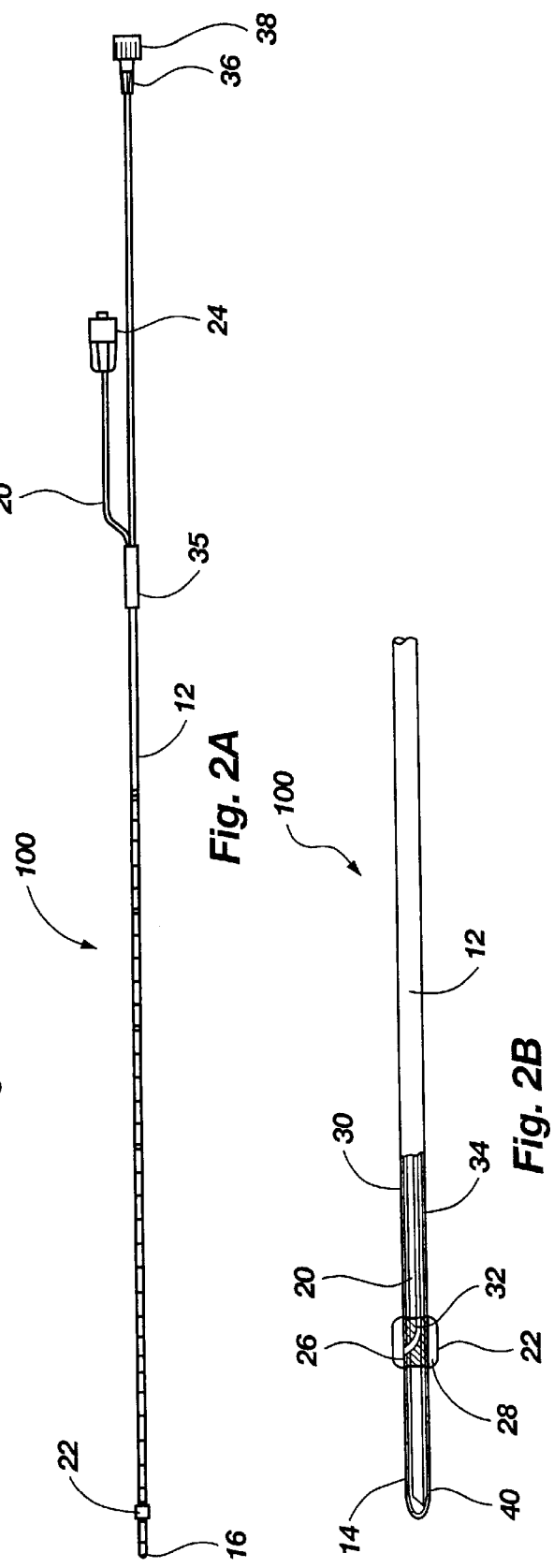

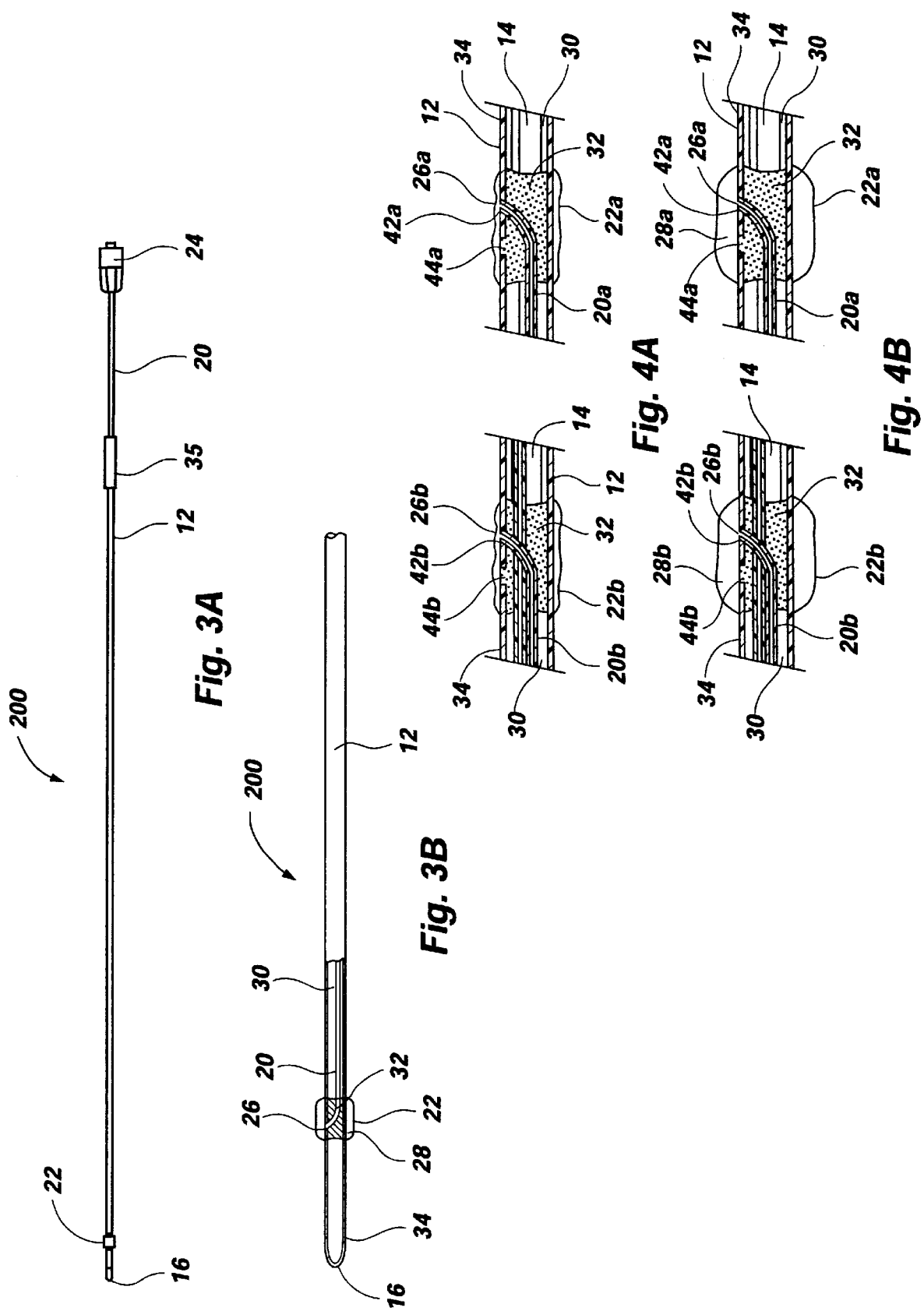

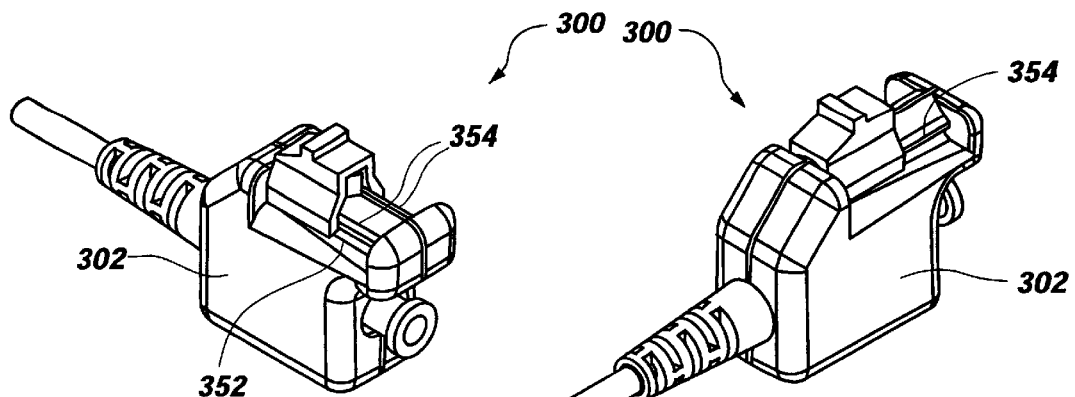
Fig. 5A
Fig. 5B
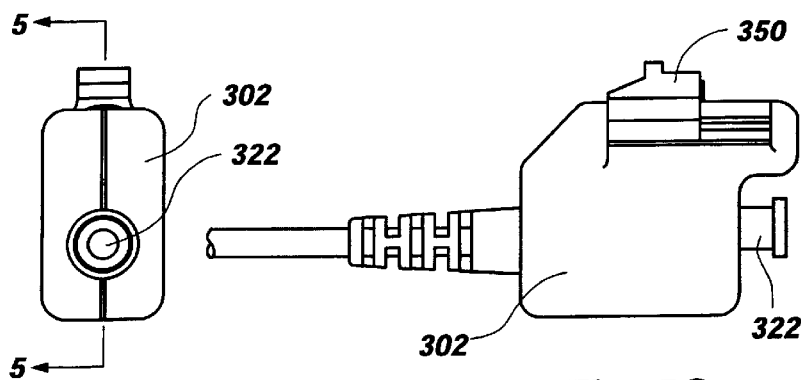
Fig. 5D
Fig. 5C
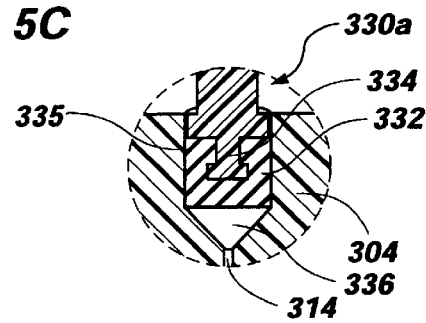
Fig. 7A
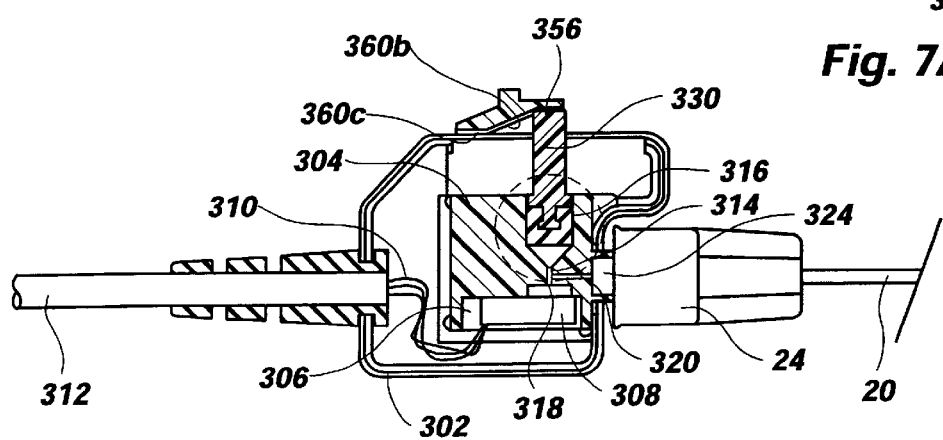
Fig. 5E

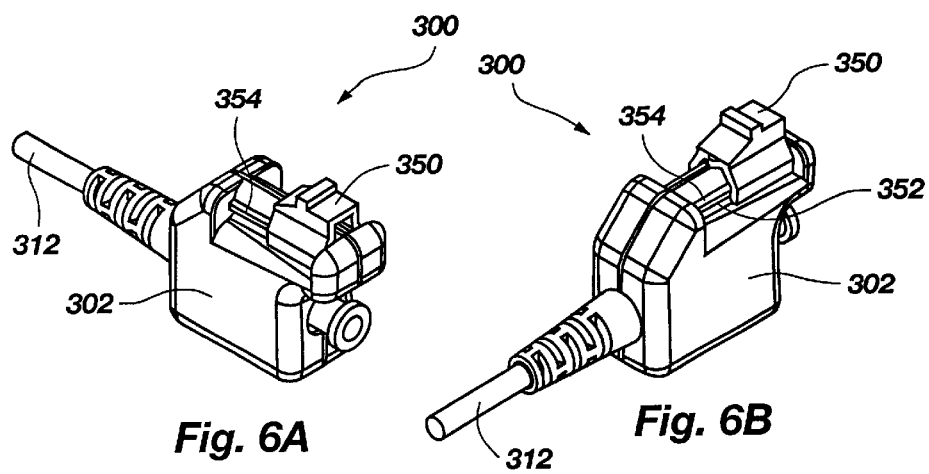
Fig. 6A    Fig. 6B
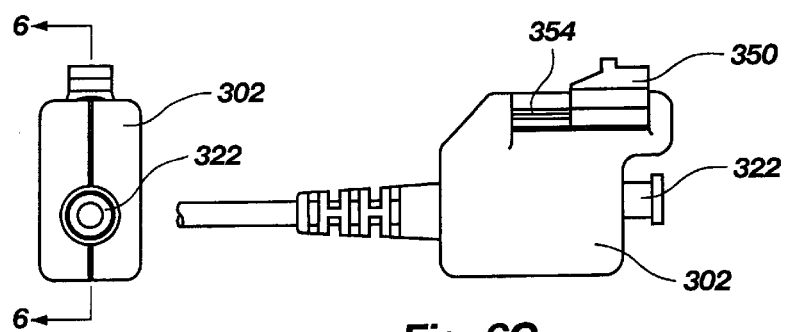
Fig. 6D    Fig. 6C
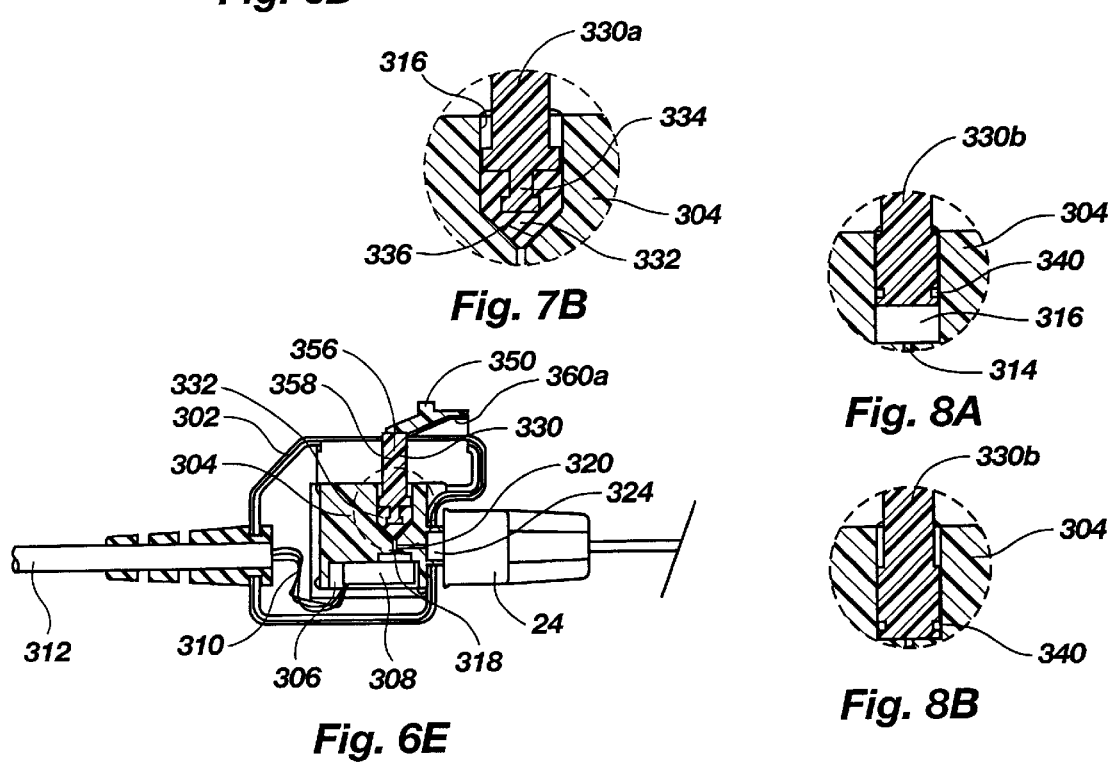
Fig. 7B
Fig. 6E
Fig. 8A
Fig. 8B

URODYNAMIC CATHETER AND METHODS OF FABRICATION AND USE

BACKGROUND OF THE INVENTION

1. Field of the Invention

The present invention relates generally to balloon-type catheters and, more specifically, to urodynamic catheters and methods of fabrication and use thereof.

2. State of the Art

A significant percentage of urinary tract disorders, particularly among women, are problems of bladder storage, or incontinence, which may be defined for purposes herein as the inability of the body to control the discharge of urine. Incontinence may result in at least a social, if not hygienic, problem, and is of significant concern to those afflicted.

Types and prevalence of incontinence among ambulatory adult women include Genuine Stress Incontinence (GSI), detrusor instability (urge incontinence), mixed incontinence (stress and urge), and other incontinence (overflow, neurogenic). The prevalence of detrusor muscle instability and of mixed incontinence has been observed to increase with age of the patient sample. Adult men have, to a lesser degree, similar incontinence problems, which are often associated with the prostate gland. Males also have urine retention issues due to the prostate.

The International Continence Society has defined GSI as "the involuntary loss of urine occurring when, in the absence of a detrusor contraction, intravesical pressure exceeds maximum urethral pressure." In other words, stress incontinence is the accidental loss of urine resulting from laughing, sneezing, coughing or even standing up; any such exertion causes abdominal pressure, as transmitted to the bladder and the urine contained therein, to exceed the resistance to flow generated by the urethra, and principally the urethral sphincter. GSI may be further categorized as hypermobility of the bladder neck and intrinsic sphincteric deficiency (ISD).

Hypermobility of the bladder neck, resulting from descent of the pelvic floor, may be attributed to weakened pelvic floor muscles and connective tissue. This phenomenon may be observed in combination with nerve damage to the external genitalia resulting from childbirth, but may occasionally be noted in younger women who have not borne children. In a normal position, the bladder is supported by the pelvic muscles, which prevent increases in abdominal pressure from exceeding urethral pressure. When the pelvic muscles are weakened or damaged, the bladder neck is abnormally displaced during abdominal stress and the urethral sphincter closure pressure becomes inadequate to maintain continence. Loss of urine due to hypermobility-related GSI typically occurs in a periodic manner and the volume of urine is somewhat proportional to the severity of the condition.

ISD is a severe form of stress incontinence which occurs due to an intrinsic deficiency of the urethral closure mechanism or due to a dysfunctional urethra wherein, in either instance, the bladder neck is open at rest. Severe ISD results in continuous leakage of urine, or leakage responsive to only minimal subject exertion. In ISD, the bladder neck may be fixed, or hypermobile. ISD occurs in a significant number of instances due to urethral scarring from past incontinence surgeries, but may result from other causes. Only a small number of patients exhibit stress incontinence attributable to ISD.

Urge incontinence is the involuntary loss of urine due to an uninhibited detrusor muscular contraction associated with a strong urge to void (detrusor instability, or DI). DI is of unknown origin, in contrast to involuntary bladder contractions attributable to a known neurological disorder, which is called detrusor hyperreflexia. Urge incontinence is frequently associated with identifiable trigger mechanisms, such as the sound or feel of running water, or during intercourse. Urine loss can be substantial, as detrusor contractions continue until the bladder is empty. An urgency to void urine responsive to abnormally low volumes during filling of the bladder during a study without other, objective evidence of detrusor overactivity is conventionally thought to be due to a hypersensitive detrusor, and is thus termed "sensory" urgency.

Mixed incontinence usually refers to a combination of GSI and DI.

A urodynamic evaluation is often employed to identify the type and magnitude of incontinence experienced by the patient, in combination with other information regarding the patient obtained from a physical examination and disclosed or documented history. Urodynamic evaluations involve measurements of the bladder pressure, generally in comparison with a reference abdominal pressure obtained by a rectal or vaginal probe, as well as measurements of urethral pressure in comparison to bladder pressure. GSI may be diagnosed during filling of the bladder, as is DI. The former is notable for a loss of urine in response to the aforementioned laughter, coughing or other "provocative" influence, while the latter is associated with involuntary, marked, periodic detrusor contractions initiating voiding. Hypermobility and ISD may be identified by the use of two different conventional diagnostic methods, the urethral pressure profile (UPP); and the valsalva leak point pressure study (VLPP study). The former procedure measures urethral pressure versus bladder pressure as a catheter is withdrawn from the bladder through the urethra. The latter procedure fills the bladder to one or more selected volumes, at which juncture the patient is requested to "bear down" slowly as if voiding to a point where leakage occurs past the catheter, or a selected bladder pressure differential over the baseline pressure is reached.

Urodynamic evaluations are employed to obtain quantitative data regarding the bladder. The aforementioned bladder filling study, or so-called "filling cystometry", measures the relationship of bladder pressure to volume of contained fluid. Bladder capacity and compliancy (the ability of the bladder to accommodate increasing volumes) is measured, as is the desire to void from a subjective, urgency standpoint. Finally, detrusor stability, or the ability of that muscle group to remain relaxed during filling of the bladder, even under the aforementioned types of provocation, is quantified.

So-called "multi-channel" cystometry is employed to correct measured bladder pressure to obtain a true bladder pressure by subtracting abdominal pressure. Bladder pressure is measured through a sensing element or port at the distal end of a catheter inserted into the bladder through the urethra, while abdominal pressure is measured by a sensing element at the distal end of a catheter inserted into the rectum or vagina of the patient. The difference in the two readings, the magnitudes of which are quantified as units of cm $H_2O$, is characterized as detrusor pressure. Monitoring the relationship between observed bladder pressure and abdominal pressure during filling of the bladder, including response to provocation, results in a cystometrogram documenting quantitative bladder function.

Various catheter designs have been employed in the art for urodynamic studies, which designs generally include a fill tube to introduce a volume of liquid into the bladder. There are three categories of catheters known to the inventors: catheters which convey bladder pressure to a transducer external to the bladder through a liquid-filled column (lumen) extending through the catheter; catheters which employ an electronic microtransducer proximate the distal ends thereof; and fiber optic transducer-tipped catheters. The two former catheter types are primarily employed in hospital urology studies and urogynecology, while the latter type is generally employed in urology and gynecology evaluations performed in a physician's office.

Existing urodynamic catheter technologies each suffer from disadvantages. For example, liquid-filled catheters require elimination of air bubbles from the liquid column extending from the entry port in the bladder to the external transducer, require hydrodynamic compensation and may be susceptible to hydrostatic influence if the external transducer and distal fill port of the catheter are not on the same horizontal plane. Electronic microtransducer- and fiber optic transducer-tipped catheters, on the other hand, are relatively expensive. In addition, fiber optic transducers require special optical/electronic interface modules. While some transducer-tipped catheters are designed for re-use, the relatively fragile transducer and catheter structures preclude the most rigorous and effective sterilization techniques and thus make confirmation of absolute sterility impossible. Due to the increasing incidence of sexually-transmitted diseases, most notably AIDS and its HIV precursor, such uncertainty is of obvious concern. Moreover, transducer-tipped catheters typically tap pressure along only a portion of the circumferential side wall of the catheter, and are thus susceptible to inaccurate and inconsistent readings during UPP procedures, as well as to missing anomalies in portions of the urethral side wall which are not traversed by a rotationally-displaced transducer during longitudinal withdrawal of the catheter through the urethra in the course of a UPP.

Thus, it would be beneficial to the art to provide a reliable, disposable, and robust yet easily manufactured catheter employing a transducer external to the patient's body which would not rely upon a liquid-filled column and which would provide an automatic "zero" or reference pressure and an accurate physiological pressure, both of which may easily be repeated as needed while the catheter remains inserted and the catheter and transducer remain assembled. It would also be desirable to provide a catheter design affording the capability for assessment of urethral sphincter function through measurement of urethral closure pressure circumferentially about the catheter as it is withdrawn from the bladder through the urethra during a UPP, so as to identify any anomalies in the urethral side wall regardless of circumferential location and to avoid false readings from such anomalies.

BRIEF SUMMARY OF THE INVENTION

The present invention comprises a disposable urodynamic catheter employing at least one thin-walled, circumferentially-extending balloon proximate the distal, or patient end thereof which communicates pressure external to the balloon proximately to a transducer external to the patient's body through a small-volume, closed air column. The catheter is inserted with the at least one balloon in a collapsed state, which is then charged after entry of the catheter into the patient's bladder, or vagina, or rectum during a multi-channel cystometry procedure.

The present invention includes at least one pressure lumen extending distally from a proximal end of an outer tubing and having an outlet terminating within the confines of a small-diameter balloon circumferentially surrounding the outer tubing at or near the distal end thereof. After insertion into the patient's body, the proximal end of the pressure lumen is connected by a disposable connector to a housing incorporating a transducer and the air column extending between the balloon and the transducer is subsequently closed and charged with a minuscule volume (for example, ~15 $\mu$liters) of air. Charging may be effectuated by an air volume displacement within the closed air column to minimize dead space therein after closure thereof. In one embodiment of the invention, two balloons independently chargeable may be employed, one proximate the distal end of the catheter and the other separated by a distance (for example, ~6 cm) proximally therefrom.

Architecture of the catheter also comprises a significant aspect of the invention. For example, the balloon is of small diameter (~0.160 inch fully inflated) and length (~0.200 inch) when inflated for enhanced coupling of urethral pressure and is extremely thin-walled, on the order of 0.0002–0.0010 inch, resulting in exceptional pliability so that wrinkles therein do not impose artifactual forces (pressures) for ideal fluid pressure transmission through the balloon membrane. Moreover, the balloon volume is heat-stabilized by using a heat-shrink material to enable shrinkage of the balloon to a fixed volume and attachment to the outer tubing by heat-shrink of the balloon end cuffs using a hot air stream, thus avoiding the need for separate heat-shrink tubing hoops or adhesives at the balloon ends and providing an extremely smooth transition between the outer tubing and balloon on the catheter exterior. A small I.D. (between about 0.005–0.008 inch) pressure lumen about eighteen to twenty-four inches long leading to the balloon provides a low internal volume relative to the balloon volume within the closed air column, ensuring acceptable frequency response and providing a relatively wide measurement range (between 0 and 250 cm $H_2O$).

Overall, the catheter is of small size, such as 7 French, and construction thereof affords good flexibility for easy insertion and added patient comfort and safety. Use of pressure lumen tubing of a different, higher durometer in comparison to the outer tubing provides a soft outer jacket and a rounded catheter distal end in combination with more rigid, less kink-prone pressure lumen tubing inside the outer tubing to achieve precision, small-bore pressure lines with a lower risk of perforation due to stiffness and less tendency to "set" in position when curled in a packaging pouch during shipment and storage prior to use. Moreover, the pressure lumen tubing is not affixed to the outer tubing except at a balloon location at a distal end of the pressure lumen tubing and where the pressure lumen tubing exits the outer tubing, promoting a flexible catheter with lower kink risk and minimizing contribution of the pressure lumen tubing to overall catheter stiffness. Similarly, a fill tube extending from the proximal end of the outer tubing to proximate a port at the distal end thereof is only secured distally to the outer tubing in the vicinity of pressure lumen tubing affixation and more proximally at an exit point of the pressure lumen tubing from the outer tubing. The use of a thin-walled, somewhat translucent material for the outer tubing permits the desirable use of UV-light curable adhesives (see below) without leaving the interior lumen tubing visible. The luer-lock (or similar) type pressure connectors employed at the proximal end of the pressure lumen tubing provide a low dead space connection and do not produce significant counter-torque on the catheter when twisted on to couple to a mating connector of the transducer housing port due to the substantially ends-only affixation of the pressure lumen tubing to the outer tubing. Further, the relative isolation of the pressure lumen tubing and fill tubing from the outer tubing provides strain relief to the former when physical stress is applied to the catheter, as mechanical loading is substantially accommodated by the outer tubing.

A tapered, interference fit connection between the cooperative luer-lock connectors of the pressure lumens and those of the reusable transducer housings minimizes dead space in the air column between the transducer and balloon. A unique, plunger-type charging structure incorporated in the transducer housing closes the air column from the ambient environment as the plunger advances beyond the extent of a relief or vent channel in the side wall of a plunger bore, and reduces dead space in the air column and charges enough air into the balloon such that pressure can be measured across the balloon membrane. In one embodiment, a deformable mass such as, for example, resilient silicone employed at an end of the plunger is compressed in a bore end as the plunger is advanced in the plunger bore, consuming column volume and providing an airtight seal at the plunger end of a passage leading to a transducer access port and a connector port. In another embodiment, a solid-ended plunger using an o-ring is employed to charge a fixed volume of air into the column and seal the passage. The configuration of the charging mechanism affords the capability for repeated, accurate one-handed closure and charging of the air column without disconnection of the catheter from the transducer housing.

During fabrication of the catheter preliminary to attachment of the balloon or balloons to the exterior of the outer tubing of the catheter, the outer tubing is formed to be round at its distal tip, then side holes or apertures are punched at the location or locations of a balloon. Then, the bladder (vesicle) filling lumen tubing and the smaller pressure lumen tubing are fed into the primary tubing for fast, easy assembly. The filling lumen tubing is fed from the proximal end until reaching the distal tip of the outer tubing. The pressure lumen tubing (two, if a two-balloon pressure sensing embodiment) is fed proximally from the punched aperture or apertures in the outer tubing side wall at the outer catheter tubing distal end and guided to exit the outer tubing through a slit in the primary tubing side wall along the proximal portion of the outer tubing. A measured volume of a UV-light curable (or alternatively an RTV) adhesive is then injected into the outer tubing bore into the side wall entry point around each pressure lumen tubing to secure the pressure lumen tubing and isolate the pressure lumen (and thus, eventually, the associated balloon) from the outer tubing bore. The adhesive is then UV-cured to secure the filling lumen tubing and pressure lumen tubing, the distal ends of the pressure lumen tubing are trimmed substantially flush with the exterior of the outer tubing, and the interior lumen tubing secured to the primary tubing in the vicinity of the slit using a collar or sleeve of heat-shrink material.

The present invention also encompasses a method of use of the catheter according to the invention, including measurement of bladder as well as, optionally, abdominal pressure using deformation of an air-filled balloon responsive to pressure on the exterior thereof to transmit pressure to a transducer external to the patient. In addition, the method of the present invention may include measurement of urethral pressure, such as, for example, during a UPP procedure, throughout an entire circumference of the catheter as it is withdrawn from the urethra.

BRIEF DESCRIPTION OF THE SEVERAL VIEWS OF THE DRAWINGS

FIGS. 1A and 1B respectively depict a side elevation of a first embodiment of a catheter according to the invention incorporating two balloons and a fill tube, and an enlarged, partial sectional side elevation of a distal end thereof;

FIGS. 2A and 2B respectively depict a side elevation of a second embodiment of a catheter according to the invention incorporating a single balloon and a fill tube, and an enlarged, partial sectional side elevation of a distal end thereof;

FIGS. 3A and 3B respectively depict a side elevation of a third embodiment of a catheter according to the invention incorporating a single balloon, and an enlarged, partial sectional side elevation of a distal end thereof;

FIGS. 4A and 4B respectively depict enlarged sectional elevations of a portion of the catheter of the first embodiment, FIG. 4A showing the balloons in an uncharged state and FIG. 4B showing the balloons in a charged state;

FIGS. 5A, 5B, 5C, 5D and 5E respectively depict a rear-quarter perspective view, a front-quarter perspective view, a side view, and a rear view of the transducer housing of the present invention and a side sectional view taken across line 5-5 in FIG. 5D with pressure lumen connected, the air column defined by the transducer and pressure lumen assembly being in the vented, or zero, position;

FIGS. 6A, 6B, 6C, 6D and 6E respectively depict a rear-quarter perspective view, a front-quarter perspective view, a side view, and a rear view of the transducer housing of the present invention and a side sectional view taken across line 6—6 in FIG. 6D with pressure lumen connected, the air column defined by the transducer and pressure lumen being in the charged, or run, position;

FIGS. 7A and 7B respectively depict an enlarged view of a first embodiment of a plunger assembly for the transducer housing as shown in FIGS. 5E and 6E in retracted and extended positions;

FIGS. 8A and 8B respectively depict an enlarged view of a second embodiment of a plunger assembly suitable for use in the transducer assembly of FIGS. 5A–E and 6A–E.

DETAILED DESCRIPTION OF THE INVENTION

Figure 9:
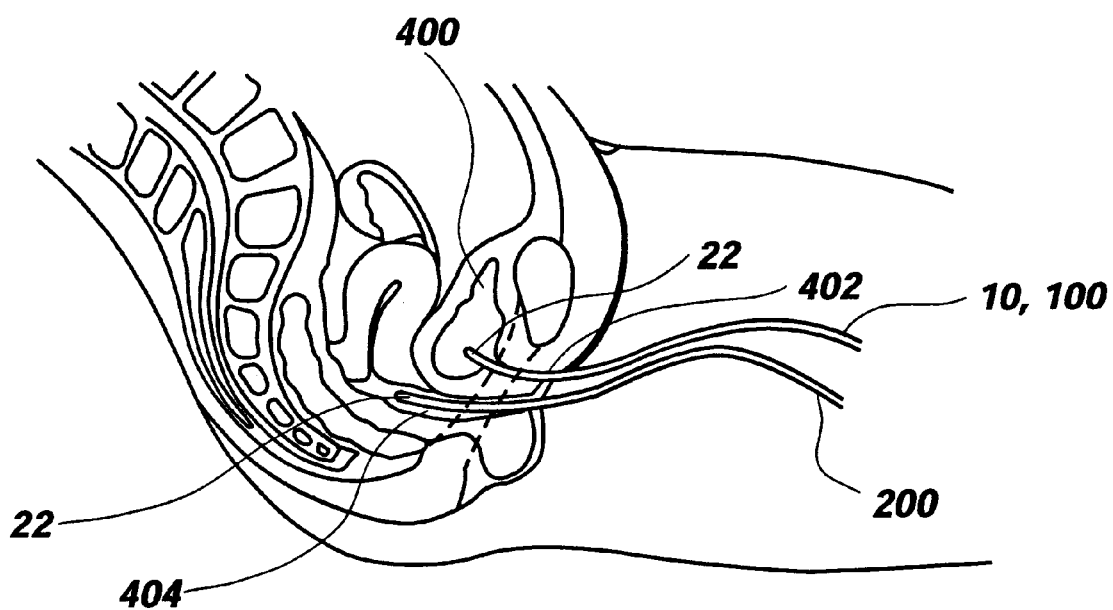
FIG. 9 is a view in partial anatomical cutaway illustrating the insertion of an embodiment of the urodynamic catheter of the present invention in the bladder of a patient and a second, reference abdominal catheter in the patient's vagina.

In the following description, the same reference numerals are employed to identify the same elements or features in various drawing figures for clarity.

Applicants hereby incorporate the disclosures of each of the following United States Patents in their entireties by this reference: Bobo, Sr., U.S. Pat. No. 5,573,007; Wallace et al., U.S. Pat. No. 5,951,497; and Wallace et al., U.S. Pat. No. 5,984,879.

Referring to FIGS. 1A and 1B in a first catheter embodiment 10 of the present invention, outer tubing 12 surrounds a fill tubing 14 extending substantially from rounded, distal end 16 of catheter 10 to proximal end 18 thereof. First and second pressure lumen tubing 20a and 20b respectively extend from distal and proximal balloons 22a and 22b, which are preferably of substantially the same size, to male luer lock connectors 24a and 24b. Balloon fill ports 26a and 26b at the distal ends of pressure tubing 20a and 20b open to the interiors 28a and 28b of balloons 22a and 22b. The distal ends of pressure tubing 20a and 20b are secured within, and balloon fill ports 26a and 26b isolated from, the bore 30 of outer tubing 12 using a mass of UV-curable adhesive 32 injected into bore 30 through the side wall 34 of outer tubing 12 adjacent the fill port locations (see FIGS. 4A and 4B for enlarged views). Pressure lumen tubing 20*a* and 20*b* may exit outer tubing 12 through a slit in the side wall 34 thereof, at which location a protective heat shrink collar or sleeve 35 is employed to secure pressure lumen tubing 20*a* and 20*b* and fill tubing 14 and prevent kinking thereof. Fill tubing 14 extends from its distal end near fill port 40 in the side wall 34 of outer tubing 12 proximally through outer tubing 12 to a female connector 36, which may comprise a luer lock or other suitable connector and which preferably has associated therewith a plug element or cap (shown) 38 for closure thereof. Fill tubing 14 is thus sealed inside of the outer tubing 12, which physically supports the fill tubing 14 and prevents it from kinking.

Referring to FIGS. 2A and 2B, a second catheter embodiment 100 of the present invention is depicted. Catheter 100 is similar to catheter 10, but includes only a single balloon 22 and associated pressure lumen tubing 20. Construction of catheter 100 is otherwise the same as that of catheter 10.

Referring to FIGS. 3A and 3B, a third catheter embodiment 200 of the present invention is depicted. Catheter 200 is similar in construction to both catheters 10 and 100, but omits the fill tubing 14 and associated female connector 36 with plug element or cap 38. Catheter 200 is configured for use as a reference, or abdominal, catheter in urodynamic procedures, placement thereof during such procedures having been previously noted above.

In the above-described embodiments, the outer tubing 12 is of 7 French (0.092 inch) diameter and formed of lubricious, soft, low durometer (~60 Shore A) polyurethane or polyethylene with EVA (ethyl vinyl acetate), and is about 45 cm in length. Balloons 22 are of ~0.3 inch in length, of ~0.0002–0.0010 inch wall thickness, and formed of polyethylene with EVA. Outer tubing 12 is preferably marked in one centimeter increments for 30 centimeters and numerical five centimeter gradations to a twenty-five centimeter mark, beginning at the distal end of the most distal balloon 22, which is ~1 cm from distal end 16 of outer tubing 12. If a second balloon is employed, as in catheter 10, it is located ~7 cm from distal end 16 of outer tubing 12. Pressure lumen tubing 20 is preferably formed of polycarbonate or other substantially rigid thermoplastic and has an I.D. of between about 0.005–0.008 inch, as previously noted, and preferably ~0.008 inch. Fill tubing is preferably formed of polyurethane or other semi-rigid thermoplastic having a durometer of Shore A and preferably has an I.D. of ~0.035 inch.

In a manner exemplary of the fabrication of catheters 10, 100 and 200, catheter 10 is formed by making a slit about 15 inches from the distal end 16 of outer tubing 12 and providing distal end 16 with a soft, rounded tip by techniques known to those of ordinary skill in the art. The exterior of outer tubing 12 is marked, as previously noted. A distal end of fill tubing 14 is notched at about a 45 degree angle (see FIGS. 1B and 2B) and inserted into outer tubing 12 from the proximal end thereof. Pressure lumen tubing 20*a* and 20*b* are inserted into outer tubing 12 through apertures 42*a* and 42*b* punched in side wall 34 at predetermined locations close to the distal end 16 of outer tubing 12 and threaded through outer tubing 12 proximally to the aforementioned slit in the side wall 34 thereof, where they exit. Then a mass of UV-curable adhesive 32 is injected into the bore 30 of outer tubing 12 through each of adhesive fill ports 44*a* and 44*b* extending through the side wall 34 of outer tubing 12 respectively adjacent apertures 42*a* and 42*b* so as to encompass the entry points of pressure lumen tubing 20*a* and 20*b* and isolate the bore 30 of outer tubing 12 therefrom (see FIGS. 4A and 4B). A suitable adhesive is UV 3321 offered by Loctite Corporation of Rocky Hill, Conn. Curing (cross-linking) of the UV-curable adhesive can be initiated in a very short time, as little as one to two seconds of exposure to UV-wavelength radiation. Curing of the adhesive also fixes the distal ends of pressure lumen tubing 20*a* and 20*b* in place, as well as fill tubing 14. The excess distal length of pressure lumen tubing 20*a* and 20*b* is trimmed substantially flush with the exterior of the side wall 34 of outer tubing 12. The proximal ends of fill tubing 14 and pressure lumen tubing 20*a* and 20*b* are sheathed with a protective sleeve or collar 35 of a heat shrink material (which is subsequently shrunken) over the area of the slit in outer tubing 12 where pressure lumen tubing 20*a* and 20*b* exits therefrom to prevent kinking, and then bonded to their respective connectors 36, 24*a* and 24*b*, as known in the art. After the balloons 22*a* and 22*b* are formed and cut, they are placed and sealingly bonded at their longitudinal ends to extend over balloon fill ports 26*a* and 26*b*, respectively, by heat-shrinking the longitudinal balloon ends, or cuffs, to the outer tubing 12 using a highly directional, hot-air stream. The balloons are baked at an elevated temperature, such as about 60° C. for about forty minutes to stabilize their respective volumes. Subsequently, a male plug element or cap 38 is placed on the fill tubing connector 36, and the catheter is leak-tested, as known in the art.

Referring to FIGS. 5A through E and 6A through E, the particulars of transducer assembly 300 according to the invention will be described. Transducer assembly 300 includes a two-piece, injection-molded plastic housing 302 which encompasses a transducer block 304 (FIGS. 7A, 7B) having transducer recess 306 within which transducer 308 is received. A suitable transducer for use with the present invention is offered by Lucas Novasensor of Fremont, Calif. Transducer 308 is powered, and sends signals to a monitor, through conductors 310 of cable 312, which extends to a monitor (not shown) as known in the art and is connected thereto with a compatible connector. Suitable monitors are offered by various companies, including without limitation Life Tech, Laborie, Dantec, MMS, Circon/Surgitek, and Brown Medical Monitors. There is preferably a Velcro® type hook patch (not shown) secured to the cable 312 or to transducer housing 302, by which the cable 312 or housing 302 may be secured to the patient's leg using a disposable Velcro® type loop adhesive patch supplied with each catheter.

Transducer block 304 includes a manifold comprising a charging and vent passage 314 extending from a plunger bore 316 to a transducer port 318 opening into transducer recess 306, transducer port 318 being faced by a sensor element, such as a diaphragm, of transducer 308, the junction of port 318 and the transducer sensor element being sealed about the periphery thereof so as to be airtight, by techniques known in the art. Pressure lumen port 320 also communicates with passage 314 and extends to the bore of female luer connector 322, which is configured to receive tapered male connector element 324 associated with a male luer lock connector 24. Plunger 330 is received within plunger bore 316 and may comprise a plunger 330a including a deformable cylindrical mass 332, such as silicone, molded over a retention head 334 (see FIGS. 7A and 7B). In this embodiment, the diameter of mass 332 may be slightly less than that of plunger bore 316, or vent grooves 335 may be formed in the plunger bore wall, the reason for which will be hereinafter explained. Further, if plunger 330a is employed, the inner end 336 of plunger bore 316 may be formed as a cone or other suitable decreasing cross-sectional shape, mass 332 being deformable thereinto responsive to inward plunger movement to charge the air column between transducer 308 and a balloon 22 with a small volume of air. Alternatively, a plunger 330b may be employed using an o-ring seal 340 about the inner end thereof (see FIGS. 8A and 8B). Again, the outer end of the bore may be enlarged to allow venting past o-ring seal 340, or vent grooves 335 may be formed in the plunger bore wall.

Saddle-shaped plunger slide 350 is disposed on the upper portion of housing 302 and retained thereon by engagement of grooves 352 with tracks 354 of housing 302. The outer end 356 of a plunger 330 extends through an aperture 358 in housing 302 between tracks 354 in a transverse orientation thereto. With plunger slide 350 in a left-most "zero" position (as depicted in FIGS. 5A through 5E), plunger 330 is in its outward-most position resting against leading inner flat 360a of plunger slide 350, and the air column defined between transducer assembly 300 and a catheter 10, 100 or 200 is vented to the ambient environment through the enlarged plunger bore portion or vent grooves 335. When plunger slide 350 is advanced to the right, as depicted in FIGS. 6A through 6E, inclined leading inner face 360b of plunger slide 350 biases plunger 330 inwardly to close the air column and charge it with a very small volume, for example 15 $\mu$liters, of air, at which point plunger 330 resides under trailing inner flat 360c of plunger slide 350. With plunger 330a, mass 332 is deformed into inner end 336 of plunger bore 316 so as to reduce volume of the air column while effecting the charge by displacing air in inner end 336 of plunger bore 316 and closing off passage 314. With plunger 330b, o-ring seal 340 closes off the air column as it advances into the inner end of plunger bore 316 inwardly of vent grooves 335 (or a narrower bore portion, as the case may be) and charges the air column by displacing air trapped in inner end of plunger bore into passage 314. FIGS. 7A and 7B are enlarged views of the plunger area of transducer block 304 with a plunger 330a respectively in zero and charged positions, while FIGS. 8A and 8B are enlarged views of the plunger area of transducer block 304 with a plunger 330b respectively in zero and charged positions.

When the air column is charged, the balloon 22 becomes at least partially filled with air, for example, 40% to 70% filled, but not completely filled, to prevent the balloon material from introducing artifact into a pressure reading. Thus, the flaccid, partially filled balloon 22 will prevent or at least significantly reduce the occurrence of aberrant effects in pressure detection due to temperature changes as dictated by Charles' Law, or other aberrant effects attributable to the balloon wall, or inadvertent, external balloon compression. The volume of air which respectively fills a balloon 22 and its associated pressure lumen 20 and transducer assembly 300 will vary, depending on balloon and lumen length and internal diameter. However, it is preferred that the volume of air in the air column is such that at least fifty percent of the volume of air in the air column will remain in balloon 22. The balloon will thus be sensitive to, and accurately transmit pressure from outside the balloon 22 to the balloon interior 28 and, through the coupling provided by the closed air column, to the transducer 308, without the introduction of artifact from the balloon wall. In the disclosed embodiment wherein a 7 French diameter catheter outer tubing 12 is employed, charging the air column with the aforementioned ~15 liters of air inflates a balloon 22 to about 0.105 inch diameter (8 French), which is believed to exhibit an accurate pressure response when employed in the urethral anatomy.

It is notable that plunger slide 350 may be manipulated by the clinician using a single hand by grasping housing 302 and moving plunger slide 350 using the thumb. It is also notable that the air column between each transducer assembly 300 and balloon or balloons 22 of a joined catheter 10, 100 or 200 may be vented, the monitor zeroed, and the air column accurately and repeatably re-charged as desired without removal of the catheter.

In use, a catheter such as 10 or 100 is inserted into a patient's bladder 400 (see FIG. 9) through the urethra 402 by techniques known in the art. Optionally, another, reference catheter 200 is inserted into the patient's rectum or vagina 404 (see FIG. 9), again as known in the art. After insertion, the pressure lumens of each catheter are respectively connected to a transducer assembly 300 in the zero, or venting mode or position, the monitor associated with each transducer assembly 300 zeroed, and then the balloons 22 charged by the aforementioned manipulation of plunger slides 350. The transducers are automatically zeroed with the transducer assembly 300 in the zero, or venting mode, as ambient atmospheric pressure acts on both sides of sensor elements, such as diaphragms, of the transducers, before the air column is closed and charged. Thus, the air column charge is thus referenced against ambient pressure. Bladder filling may then be commenced through a fill tubing 14, with attendant pressure data being accumulated by a monitor or monitors to which transducer assemblies are 300 connected by cables 312, as known in the art. Other, conventional maneuvers may be performed, such as a VLPP study, again as known in the art. As bladder (or abdominal) pressure increases, deformation of a balloon 22 modifies pressure in its associated air column, which is transmitted to the transducer sensor element, such as a diaphragm, through the pressure lumen extending therebetween. Response of the sensor element to the pressure variation generates an electrical or other signal which is relayed to a monitor through the transducer cable 312.

If a UPP procedure is to be initiated, a catheter 10 carrying two balloons 22 will be used. As known in the art, urethral pressure will be measured during withdrawal of catheter 10 from the bladder through the urethra using the most proximal balloon 22b, while bladder pressure is monitored using balloon 22a at the distal end 16 of outer tubing 12. As noted previously, the circumferential envelopment of outer tubing 12 of balloon 22b provides a pressure responsive element for effecting an accurate measurement of urethral pressure and urethral sphincter strength and integrity regardless of small anatomical anomalies of the urethra. Further, the presence of any such anomalies is more easily identified due to the circumferential contact of the balloon 22b with the urethral wall than by prior art, single reference, pin-point localized transducer elements such as micro-transducers and fiber optic transducers.

While the present invention has been described with reference to certain illustrated embodiments, those of ordinary skill in the art will recognize and appreciate that it is not so limited. Accordingly, additions, deletions and modifications to the embodiments of the invention as disclosed may be effectuated without exceeding the scope of the invention as encompassed by the claims following hereinafter.

What is claimed is:

1. A catheter system for use in detecting pressure changes within a body, comprising:

an elongated tube having at least one lumen extending therethrough to a port located proximate a distal end thereof;

a pressure-compliant balloon element secured to the elongated tube over the port and having an interior in communication therewith;

a pressure transducer removably operably coupled to a proximal end of the at least one lumen and including a sensor element in communication with an interior of the pressure-compliant balloon element through the at least one lumen; and a charging structure for displacing a substantially predetermined volume of air into an air column extending between the pressure-compliant balloon element and the pressure transducer sensor element through the at least one lumen, the charging structure being configured, while the pressure transducer is operably coupled to the proximal end of the at least one lumen, to vent the air column to an ambient environment in a first mode, and to close the air column and effect displacement of the substantially predetermined volume of air in a second mode.

2. The catheter system of claim 1, wherein the charging structure includes a plunger longitudinally movable in a bore in communication with the air column, the plunger and bore being cooperatively configured to provide venting clearance between a side of the plunger and an interior wall of the bore in a first longitudinal plunger position, and to mutually seal in airtight relationship in a second longitudinal plunger position.

3. The catheter system of claim 2, wherein the venting clearance is provided by a portion of the interior wall of the bore including a longitudinally extending groove therein.

4. The catheter system of claim 2, wherein the first longitudinal plunger position comprises a relatively retracted position, and the second longitudinal plunger position includes a relatively extended position.

5. The catheter system of claim 4, wherein an end of the plunger received within the bore includes a deformable mass.

6. The catheter system of claim 5, wherein at least a portion of an inner end of the bore contracts to a relatively smaller cross-section, and the deformable mass is deformed into the at least a portion of the inner end of the bore in the second longitudinal plunger position.

7. The catheter system of claim 4, wherein the plunger includes a circumferential seal thereabout.

8. The catheter system of claim 4, wherein the charging structure further includes a movable plunger slide engageable with an outer end of the plunger to effect movement thereof between the first longitudinal plunger position and the second longitudinal plunger position.

9. The catheter system of claim 2, wherein the proximal end of the at least one lumen, the charging structure and the pressure transducer sensor element are in mutual communication through passages in a manifold block housing the bore, to which the pressure transducer is secured, and which includes a connector element configured for engagement with a connector element at the proximal end of the at least one lumen.

10. The catheter system of claim 9, wherein the charging structure and the pressure transducer are substantially contained within a housing on which is slidably mounted a plunger slide positioned and configured to move the plunger between the first longitudinal plunger position and the second longitudinal plunger position.

11. The catheter system of claim 10, wherein the plunger slide is oriented for movement substantially transverse to an orientation of the plunger and to traverse a path extending over the plunger to effect movement of the plunger between the first longitudinal plunger position and the second longitudinal plunger position by mutual contact of the plunger slide and the plunger.

12. The catheter system of claim 10, wherein the housing is sized and configured and the plunger slide is placed on the housing in a position to permit manipulation of the plunger slide with a thumb of a hand grasping the housing.

13. A catheter for use in detecting pressure changes within a body, comprising:

an elongated outer tubing element comprising a bore defined within a circumferential side wall thereof;

at least one elongated pressure lumen tubing element extending at least partially within the bore of the elongated outer tubing element, extending through the side wall thereof proximate a distal end thereof and defining a port opening onto the side wall exterior;

a cured adhesive mass disposed within the bore where the at least one elongated pressure lumen tubing element extends through the side wall, securing the at least one elongated pressure lumen tubing element in place and sealing the bore from the side wall exterior; and a pressure-compliant balloon element circumferentially surrounding the elongated outer tubing element, extending over the port of the at least one elongated pressure lumen tubing element and sealingly bonded to the side wall proximally and distally of the port.

14. The catheter of claim 13, wherein the cured adhesive mass is selected from the group comprising a UV-curable adhesive and an RTV adhesive.

15. The catheter of claim 13, wherein the pressure-compliant balloon element is formed of a heat-shrink material.

16. The catheter of claim 15, wherein the pressure-compliant balloon element is sealingly bonded to the side wall of the elongated outer tubing element by heat-induced contraction of ends of the pressure compliant balloon element about the elongated outer tubing element.

17. The catheter of claim 16, wherein a volume of the pressure-compliant balloon element has been stabilized by temperature elevation of the heat-shrink material.

18. The catheter of claim 13, wherein the elongated outer tubing exhibits a durometer lower than a durometer of the at least one elongated pressure lumen tubing element.

19. The catheter of claim 13, wherein the at least one elongated pressure lumen tubing element remains substantially unsecured to the elongated outer tubing element between a location of the cured adhesive mass and an exit location of the at least one elongated pressure lumen tubing element from the outer tubing element bore.

20. The catheter of claim 13, further including at least one fill tubing element extending at least in part through the bore of the elongated outer tubing element to a location proximate the distal end thereof and in communication with an exterior of the elongated outer tubing element through at least one aperture in the side wall, the at least one fill tubing element passing through the cured adhesive mass and being fixed in the bore thereby.

21. The catheter of claim 20, wherein the at least one elongated pressure lumen tubing element comprises two elongated pressure lumen tubing elements extending through the side wall of the elongated outer tubing element at longitudinally separated locations.

22. The catheter of claim 13, further including:

a pressure transducer removably operably coupled to a proximal end of the at least one elongated pressure lumen tubing element and including a sensor element in communication with an interior of the pressure-compliant balloon element through the at least one elongated pressure lumen tubing element; and a charging structure for displacing a substantially predetermined volume of air into an air column extending between the pressure-compliant balloon element and the pressure transducer sensor element through the at least one elongated pressure lumen tubing element, the charging structure being configured, while the transducer is operably coupled to the proximal end of the at least one elongated pressure lumen tubing element, to vent the air column to an ambient environment in a first mode, and to close the air column and effect displacement of the substantially predetermined volume of air in a second mode.

23. The catheter of claim 22, wherein the charging structure includes a plunger longitudinally movable in a bore in communication with the air column, the plunger and bore being cooperatively configured to provide venting clearance between a side of the plunger and an interior wall of the bore in a first longitudinal plunger position, and to mutually seal in airtight relationship in a second longitudinal plunger position.

24. The catheter of claim 23, wherein the venting clearance is provided by a portion of the interior wall of the bore including a longitudinally extending groove therein.

25. The catheter of claim 23, wherein the first longitudinal plunger position comprises a relatively retracted position, and the second longitudinal plunger position includes a relatively extended position.

26. The catheter of claim 25, wherein an end of the plunger received within the bore includes a deformable mass.

27. The catheter of claim 26, wherein at least a portion of an inner end of the bore contracts to a relatively smaller cross-section, and the deformable mass is deformed into the at least a portion of the inner end of the bore in the second longitudinal plunger position.

28. The catheter of claim 25, wherein the plunger includes a circumferential seal thereabout.

29. The catheter of claim 25, wherein the charging structure further includes a movable plunger slide engageable with an outer end of the plunger to effect movement thereof between the first longitudinal plunger position and the second longitudinal plunger position.

30. The catheter of claim 23, wherein the proximal end of the at least one elongated pressure lumen tubing element, the charging structure and the pressure transducer sensor element are in mutual communication through passages in a manifold block housing the bore, to which the pressure transducer is secured, and which includes a connector element configured for engagement with a connector element at the proximal end of the at least one elongated pressure lumen tubing element.

31. The catheter of claim 30, wherein the charging structure and the pressure transducer are substantially contained within a housing on which is slidably mounted a plunger slide positioned and configured to move the plunger, responsive to movement of the plunger slide, between the first longitudinal plunger position and the second longitudinal plunger position.

32. The catheter of claim 31, wherein the plunger slide is oriented for movement substantially transverse to an orientation of the plunger and to traverse a path extending over the plunger to effect movement of the plunger between the first longitudinal plunger position and the second longitudinal plunger position by mutual contact of the plunger slide and the plunger.

33. The catheter of claim 31, wherein the housing is sized and configured, and the plunger slide is placed on the housing in a position to permit manipulation of the plunger slide with a thumb of a hand grasping the housing.

34. The catheter of claim 23, wherein the plunger and bore are sized and cooperatively configured to provide a charge of ~15 $\mu$liters of air to the air column when the plunger is in the second longitudinal plunger position.

35. The catheter of claim 34, wherein the elongated outer tubing element is of about 7 French diameter and the balloon element exhibits a diameter of about 8 French when the air column is charged.

36. The catheter of claim 13, wherein the at least one elongated pressure lumen tubing element has an inner diameter of about 0.005 to 0.010 inch.

37. The catheter of claim 13, wherein the elongated outer tubing element has an outer diameter of about 7 French.

38. A method for conducting a urodynamic procedure, comprising:

inserting an end of a catheter carrying a pressure responsive element into a patient's bladder through the patient's urethra;

at least partially inflating the pressure responsive element with air such that the pressure responsive element is in substantially complete circumferential contact with an interior of the urethra;

adding fluid to the patient's bladder through the catheter to elevate bladder pressure; and withdrawing the catheter from the patient's bladder through the urethra while measuring the bladder pressure and measuring urethral pressure using the pressure responsive element in substantially complete circumferential contact with the interior of the urethra during the withdrawal of the catheter.

39. The method of claim 38, wherein using a pressure responsive element in substantially complete circumferential contact with the interior of the urethra comprises using a balloon element extending circumferentially about the catheter.

40. The method of claim 39, wherein measuring the urethral pressure further comprises substantially continuously transmitting air pressure in the balloon element through a closed air column to a transducer located external to the patient while withdrawing the catheter.

41. A method of fabricating a catheter including at least one pressure lumen and an associated balloon element, the method comprising:

forming an aperture in a side wall of an elongated tubing element proximate a distal end thereof;

inserting an elongated pressure lumen tubing element of smaller diameter than the elongated tubing element through the side wall aperture into a bore of the elongated tubing element and threading the elongated pressure lumen tubing element proximally through the bore to a desired location;

introducing an adhesive mass into the bore of the elongated tubing element to surround the aperture and the elongated pressure lumen tubing element; and curing the adhesive mass.

42. The method of claim 41, further comprising:

removing a portion of the elongated pressure lumen tubing element extending through the aperture and outside the elongated tubing element;

placing a sheath of heat-shrinkable material over the aperture to extend distally and proximally therefrom; and heat-shrinking distal and proximal ends of the sheath to sealingly bond the ends to the distal and proximal elongated tubing element to define a balloon extending circumferentially thereabout.

43. The method of claim 42, further comprising threading an elongated fill tubing element distally from a proximal end of the elongated tubing element to a location proximate the distal end thereof before introducing the adhesive mass.

44. The method of claim 43, further including forming another aperture through the side wall of the elongated tubing element at a location longitudinally spaced therefrom, inserting a second elongated pressure lumen tubing element into the bore through the another aperture and threading the second elongated pressure lumen tubing element proximally to the desired location, introducing another adhesive mass into the bore of the elongated tubing element to surround the another aperture and the second elongated pressure lumen tubing element and curing the another adhesive mass.

45. The method of claim 44, further comprising:

removing a portion of the second elongated pressure lumen tubing element extending through the another aperture and outside the elongated tubing element;

placing a second sheath of heat-shrinkable material over the another aperture to extend distally and proximally therefrom; and heat-shrinking distal and proximal ends of the second sheath to sealingly bond the distal and proximal ends of the second sheath to the elongated tubing element to define a second balloon extending circumferentially thereabout.

46. The method of claim 45, further comprising subjecting the sheath and the second sheath to an elevated temperature for a selected period of time to stabilize an internal volume of the balloon and the second balloon.

47. The method of claim 46, wherein curing the adhesive mass and the another adhesive mass is effected by exposure to UV wavelength radiation.

48. The method of claim 42, further comprising subjecting the sheath to an elevated temperature for a selected period of time to stabilize an internal volume of the balloon.

49. The method of claim 41, wherein curing the adhesive mass is effected by exposure to UV radiation.

* * * * *

UNITED STATES PATENT AND TRADEMARK OFFICE
CERTIFICATE OF CORRECTION

PATENT NO. : 6,447,462 B1
DATED : September 10, 2002
INVENTOR(S) : Wm. Dean Wallace et al.

It is certified that error appears in the above-identified patent and that said Letters Patent is hereby corrected as shown below:

Title page,
Item [56], References Cited, U.S. PATENT DOCUMENTS, change "4,019,505" to -- 4,019,515 --.

Column 10,
Line 25, change "are 300" to -- 300 are --

Signed and Sealed this

Twenty-third Day of December, 2003

JAMES E. ROGAN
*Director of the United States Patent and Trademark Office*